Figure 1:
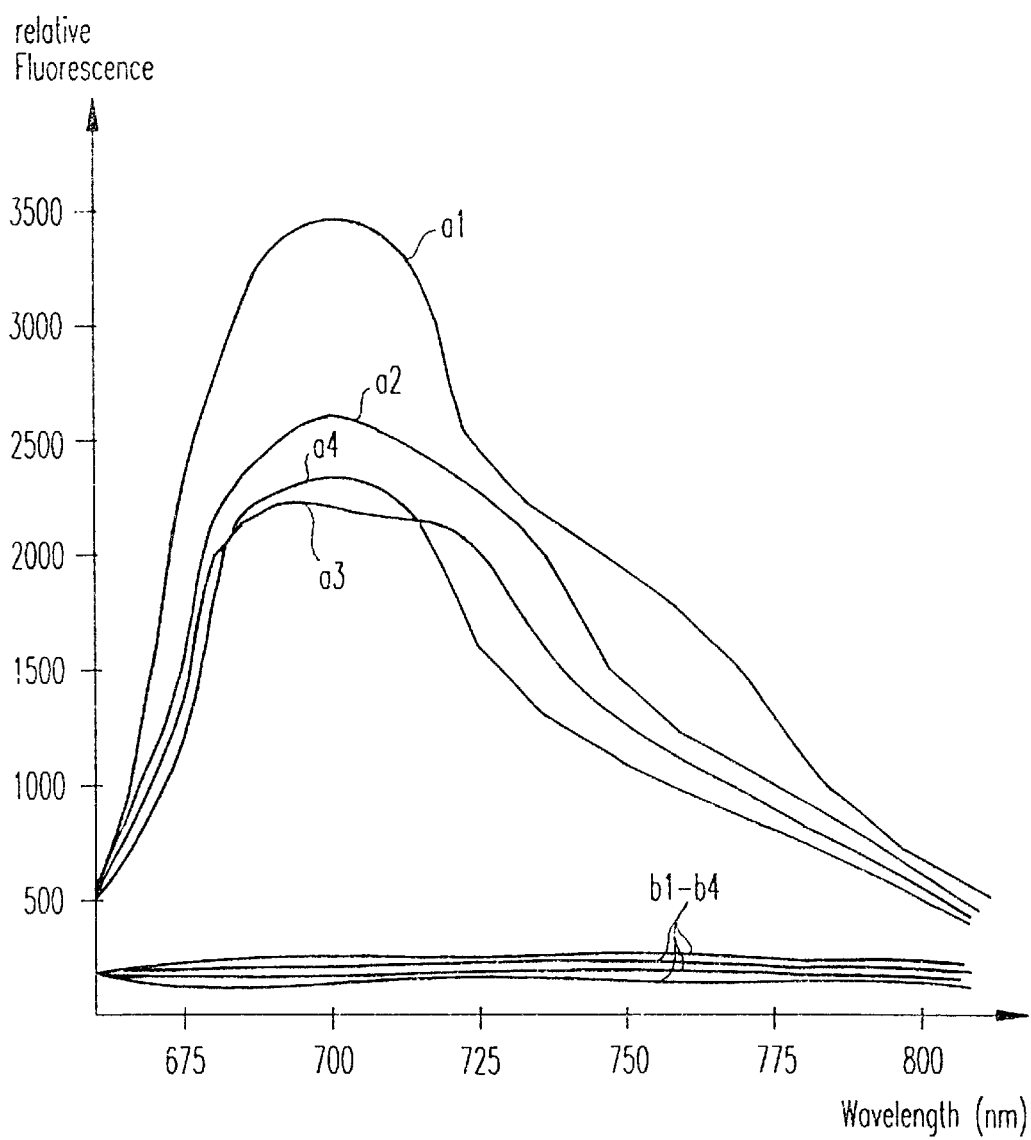

United States Patent

Hibst et al.

[11] Patent Number: 6,024,562
[45] Date of Patent: Feb. 15, 2000

[54] DEVICE FOR THE RECOGNITION OF CARIES, PLAQUE OR BACTERIAL INFECTION ON TEETH

[75] Inventors: Raimund Hibst, Erbach; Robert Gall, Augsburg; Mario Klafke, Mainaschaff, all of Germany

[73] Assignee: Kaltenbach & Voigt GmbH & Co., Biberach am Riss, Germany

[21] Appl. No.: 08/744,019

[22] Filed: Nov. 5, 1996

[30] Foreign Application Priority Data

Nov. 8, 1995 [DE] Germany ............... 195 41 686

[51] Int. Cl.$^7$ .......................................... A61C 1/00
[52] U.S. Cl. ................................. 433/29; 128/665
[58] Field of Search ............ 433/29, 215; 128/665; 356/317, 318, 341

[56] References Cited

U.S. PATENT DOCUMENTS

| | | | |
|---|---|---|---|
| 4,479,499 | 10/1984 | Alfano | 433/29 |
| 4,515,476 | 5/1985 | Ingmar | 128/665 |
| 5,111,821 | 5/1992 | Potter | 128/665 |
| 5,198,871 | 3/1993 | Hill, Jr. et al. | 356/318 |
| 5,306,144 | 4/1994 | Hibst et al. | 433/29 |
| 5,382,163 | 1/1995 | Putnam | 433/29 |

FOREIGN PATENT DOCUMENTS

| | | |
|---|---|---|
| 3031249 C2 | 11/1986 | Germany. |
| 4200741 A1 | 7/1993 | Germany. |

OTHER PUBLICATIONS

E. de Josselin de Jong et al. (1995) "New Method for in vivo Quantification of Changes in Initial Enamel Caries with Laser Fluorescence", *Caries Res.* 29:2–7.

S. Albin (1988) "Laser Induced Fluorescence of Dental Caries", *SPIE* 907:96–99.

*Primary Examiner*—Cary E. O'Connor
*Attorney, Agent, or Firm*—Scully, Scott, Murphy & Presser

[57] ABSTRACT

A device for the recognition of caries, plaque or bacterial infection on teeth, which includes a light source for generating an excitation radiation which is to be directed onto a tooth to be investigated and producing an fluorescence radiation at the tooth. Also included is a detection device for detecting the fluorescence radiation of the tooth, and a spectral filter arranged in front of the detection device, wherein the wavelength of the excitation radiation emitted from the light source lies within the range of between 640 and 670 nm.

9 Claims, 3 Drawing Sheets

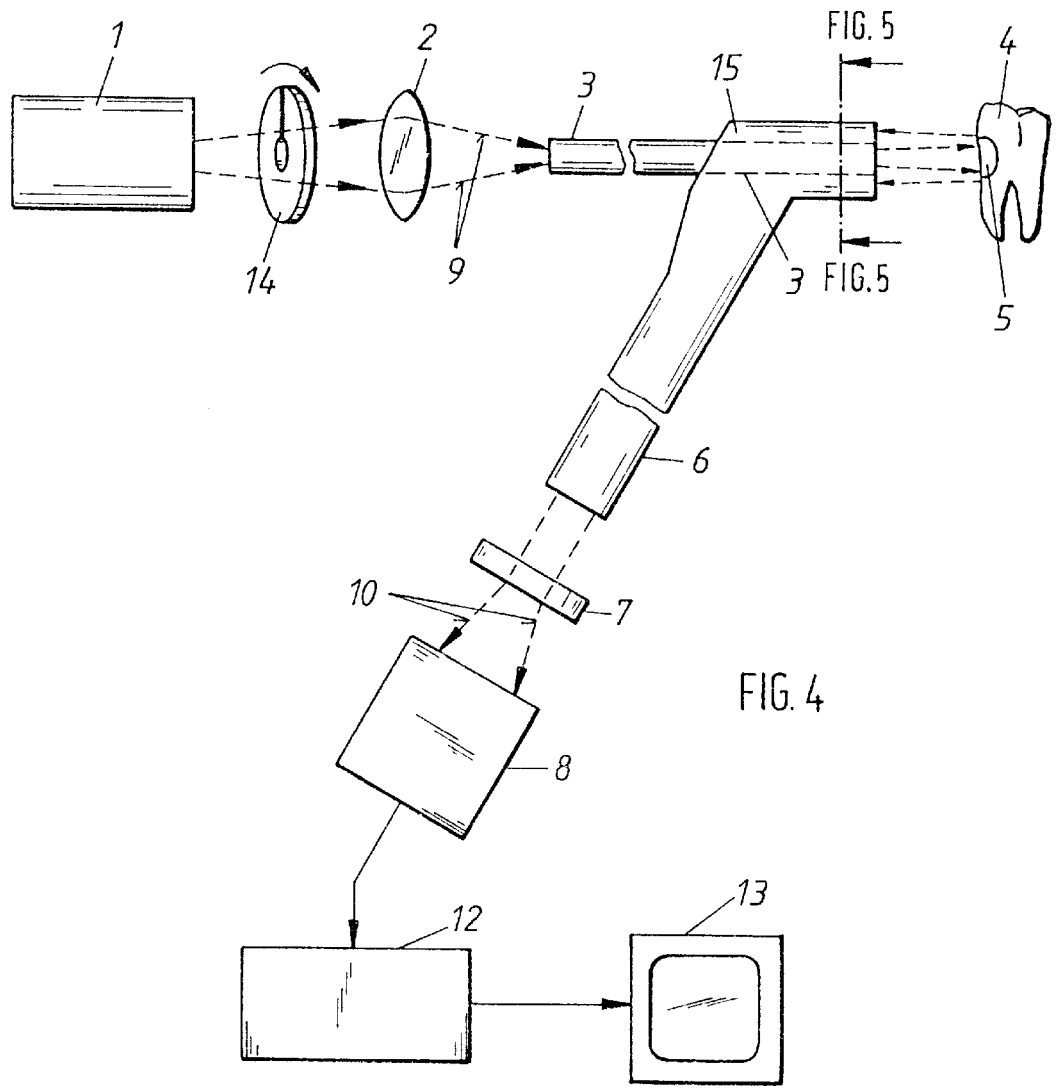
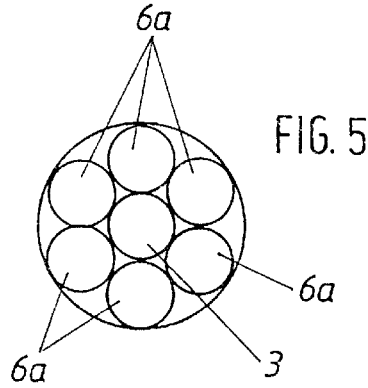
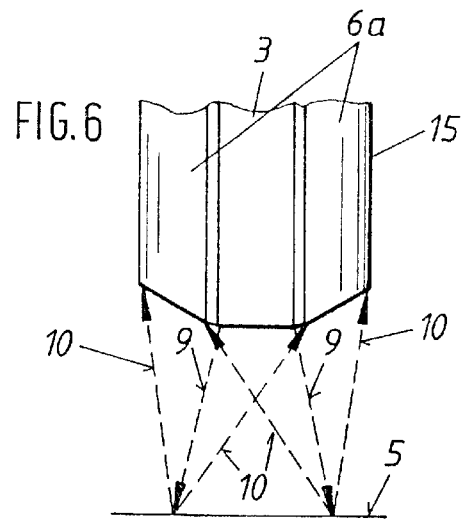

DEVICE FOR THE RECOGNITION OF CARIES, PLAQUE OR BACTERIAL INFECTION ON TEETH

The invention relates to a device for the recognition of caries, plaque or bacterial infection on teeth.

It is known to reveal caries, plaque or bacterial infection on teeth by means of visual examination or by means of the employment of X-rays. However, with a visual examination satisfactory results frequently cannot be achieved, since for example caries in the early stage or at a tooth region which is difficult to observe cannot be detected. Although, on the other hand, X-rays have proved to be a very effective way of detecting an occurrence of caries or other tooth diseases, this method of examination also is not optimal because of the damaging effects of the X-rays on human health. There was thus a need for the development of a new technique for enabling the detection of the presence of caries in teeth.

In DE 30 31 249 C2 a contactless method of examination for detection of caries in human teeth was proposed whereby the tooth is irradiated with virtually monochromatic light. The virtually monochromatic light radiation excites a fluorescence radiation at the tooth. Thereby it was discovered that the fluorescence spectrum reflected from the tooth exhibits clear differences between carious and healthy regions of the tooth. Thus, in the red spectral region of the fluorescence spectrum of the tooth (ca. 550 to 650 nm) the intensity is significantly higher than with a healthy tooth. In contrast, in the blue spectral region of the reflected fluorescence spectrum of the tooth (ca. 350 to 450 nm) the intensity of the fluorescence radiation is virtually identical for carious regions and healthy regions of the tooth. DE 30 31 249 C2 proposes the irradiation of the tooth for example with a wavelength of 410 nm and by means of two filters to detect the fluorescence radiation of the tooth for a first wavelength of 450 nm and for a second wavelength of 610 nm, i.e. in blue and red spectral regions, by means of photodetectors. The fluorescence radiation intensities detected by means of this arrangement are subtracted so that on the basis of the difference intensity thereby derived a healthy tooth region can be unambiguously distinguished from a carious tooth region.

The same method is described in S. Albin et al, "Laser Induced Fluorescence of Dental Caries", Proc SPIE 907, pages 96–98, 1988, whereby, however, an excitation wavelength of 488 nm is proposed.

DE 42 00 741 A proposes, as an advantageous further development, to bring about the fluorescence of the tooth by means of an excitation radiation having a wavelength in the range 360 to 580 nm and to filter out the fluorescence radiation of the tooth for wavelengths from 620 nm. By means of these measures, the difference between the wavelength of the excitation radiation and the received fluorescence radiation is sufficiently great that the excitation radiation cannot, through superimposition on the fluorescence radiation, distort the evaluation results.

In the paper by E. de Josselin de Jong et al, "A new Method for in vivo Quantification of Changes in Initial Enamel Caries with Laser Fluorescence", Caries Res 1995, 29, pages 2–7, it is proposed to irradiate the tooth with laser light having a wavelength from 488 nm and to detect the fluorescent radiation of the tooth for wavelengths from 520 nm via a CCD camera and to evaluate it by means of a computer program, in order to be able to detect carious tooth regions.

The above-described known methods of examination and devices have in common that for the excitation of the fluorescence of the tooth an excitation radiation having a wavelength less than 580 nm is employed. By these means, although on the one hand a relatively high effective cross-section for the generation of the fluorescence radiation can be obtained, the fluorescence radiation for healthy tooth tissue is however significantly stronger than that from carious lesions. Thus, with the known methods of examination and devices there is necessary a complex direct comparison of fluorescence radiation, in a particular wavelength range, emitted from neighbouring healthy and carious regions (see e.g. E. de Josselin de Jong et al) or the measurement signals of fluorescence radiation detected in two differing wavelength regions must be compared with one another in a complicated manner (cf e.g. DE 30 31 249 C2). Further, the above-described known devices require a complicated construction, so that these apparatuses cannot be manufactured economically and thus have scarcely established themselves in the marketplace.

In general, with reducing wavelength of excitation radiation, the scattering of light in the tooth tissue increases. With regard to the known devices and methods, this leads to a further problem since because of the small wavelength of the excitation radiation with the known devices and the strong light scattering brought about thereby only tooth surface regions directly illuminated by the excitation radiation can be examined.

Thus, the object of the invention is to provide a device for the recognition of caries, plaque or bacterial infection on teeth which allows a reliable detection of caries, plaque or bacterial infection at tooth regions which cannot be directly observed or reached, and which has a high sensitivity. Further, the device should be simple, economical and not susceptible to problems.

This object is achieved by the characterising features of claim 1.

Advantageous configurations of the invention are described in the subclaims.

In accordance with the invention the wavelength of the excitation light, emitted from a light source, for the excitation of fluorescence at the teeth, is between 600 nm and 670 nm. The fluorescence radiation of the tooth is detected via a filter, whereby in accordance with the invention the filter has a pass range for wavelengths greater than 670 nm.

The invention is based on experimental results which have shown that also with an excitation radiation in the red spectral range (that is, with a wavelength between 600 nm and 670 nm) in the case of bacterial infection of teeth, in particular in the case of caries, the fluorescence radiation of the teeth can be excited. Excitation with a radiation in the above-mentioned wavelength range has the advantage, with regard to the state of the art, that the fluorescence radiation from healthy tooth regions is strongly reduced at such excitation wavelengths. By these means, the fluorescence radiation from carious regions is only very slightly superimposed with the autofluorescence of the healthy tooth tissue, so that caries, plaque or bacterial infection on teeth can be recognized simply, in a manner not susceptible to problems, and with high sensitivity. Thus, the device in accordance with the invention is ideally suited for the early diagnosis of caries or bacterial infection on teeth.

Further, there can be employed for the evaluation of the fluorescence radiation, in contrast to the state of the art, not only a relatively narrow spectral region of the fluorescence radiation but the very broad spectral range for wavelengths greater than 670 nm. For the detection of the fluorescence radiation, because of the high sensitivity of the device in accordance with the invention, there no longer need to be employed complex CCD cameras or high sensitivity photomultipliers; rather there can be employed for detection of the fluorescence radiation of the tooth, as light sensitive elements, simple photodiodes. A further advantage of the invention lies in that for the wavelength range of the excitation light in accordance with the invention and for the fluorescence radiation detected by means of the filter, the scattering in the tooth tissue can be kept very slight, so that even caries in tooth regions which are difficult to observe or reach, for example caries in the regions between teeth or undermining carious lesions, can be reliably recognized in a simple manner. Finally, it is also advantageous that in accordance with the invention simple light sources, e.g. laser diodes, can be employed, so that a complex collimator optical system is no longer necessary. Likewise, a simple battery operation is possible.

Figure 2:
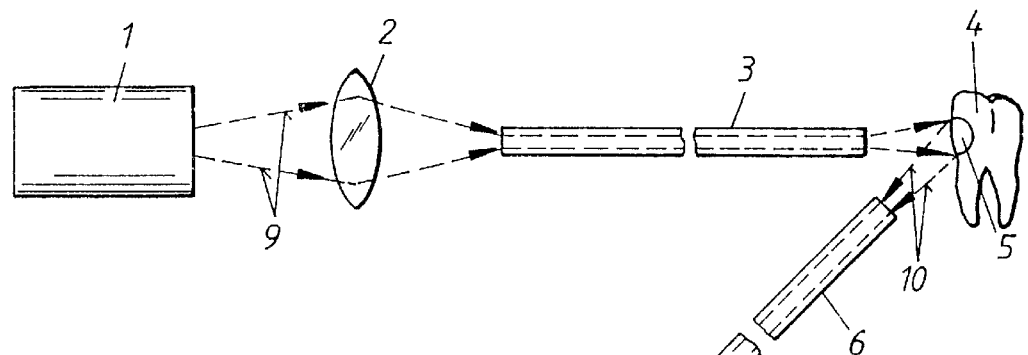
Figure 3:
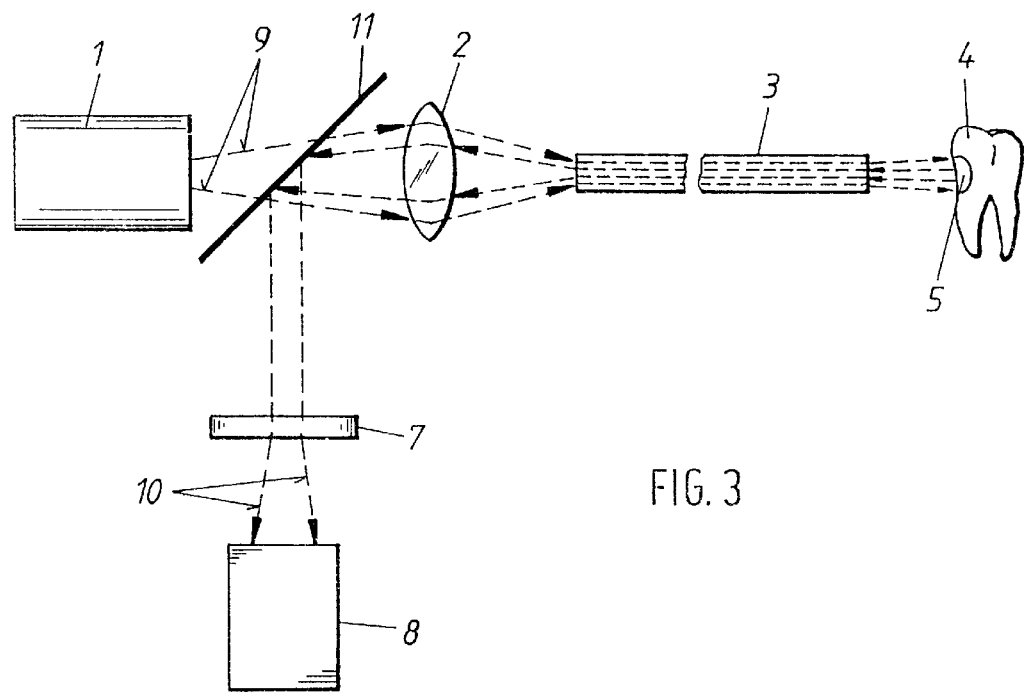

The invention will be described in more detail with reference to the drawings and with reference to advantageous exemplary embodiments. There is shown:

FIG. 1 exemplary fluorescence spectrums for carious and healthy tooth tissue in the case of employment of the device in accordance with the present invention, FIG. 2 a first exemplary embodiment of the device in accordance with the invention, FIG. 3 a second exemplary embodiment of the device in accordance with the invention, FIG. 4 a third exemplary embodiment of the device in accordance with the invention, FIG. 5 a cross-sectional view of a light conductor of the device in accordance with the invention, and FIG. 6 a side-view of the end region, towards the tooth, with an advantageous configuration of the light conductor illustrated in FIG. 5.

FIG. 1 shows exemplary fluorescence spectrums of the tooth tissue in the case of employment of the device in accordance with the invention. The fluorescence spectrums designated a1 represent the fluorescence spectrums of carious regions and those designated b1 represent the fluorescence spectrums of healthy tooth tissues. The fluorescence spectrums were obtained through generation of an excitation radiation by means of a dye laser for the excitation wavelength 620 nm (fluorescence spectrums a1 and b1), 630 nm (fluorescence spectrums a2 and b2), 640 nm (fluorescence spectrums a3 and b3) and 650 nm (fluorescence spectrums a4 and b4). For the fluorescence spectrums illustrated in FIG. 1 the laser power was 60 mW. From FIG. 1 it can be seen that because of the excitation wavelength range between 600 nm and 670 nm proposed in accordance with the invention, and the configuration of the fluorescence radiation of the tooth for wavelengths greater than 670 nm in accordance with the invention, there is provided a very great difference between the fluorescence intensity for carious regions and the fluorescence intensity for healthy tooth regions. The fluorescence spectrum detected for wavelengths greater than 670 nm can thus be directly and simply evaluated in accordance with the invention, so that directly on the basis of the detected fluorescence carious regions can be determined to exist. The very complex evaluation procedures known from the state of the art are thus no longer necessary with the device in accordance with the invention.

FIG. 2 shows a first exemplary embodiment of the device in accordance with the invention. A light source 1 generates an excitation radiation 9 which is delivered to a region 5 of the tooth 4 to be investigated via a coupling lens system 2 and a light conductor. Through the excitation radiation having a wavelength in the range 600 nm to 670 nm there is caused in the irradiated tooth region 5 a fluorescence radiation 10 over a relatively wide spectral range, which fluorescence radiation is delivered via a second light conductor 6 and a spectral filter 7 to a detection device 8 for detection and evaluation of the fluorescent radiation of the tooth. Thereby, the spectral filter is preferably so configured that it passes only fluorescence radiation having a wavelength greater than 670 nm. The detection device 8 directly evaluates the fluorescence radiation 10 delivered thereto and determines directly from the detected fluorescence radiation 10 the presence or absence of caries, plaque or bacterial infection.

The light source 1 is preferably a HeNe-laser or a laser diode which generates the excitation radiation having a wavelength in the range 600 nm to 670 nm. Thereby, the available output power of these laser diodes increases with increasing wavelength, and the cost reduces. Against this, with increasing excitation wavelength the spectral difference between the excitation wavelength and the fluorescence radiation reduces, so that the demands made upon the filter are increased. As a compromise, in particular an excitation wavelength of ca. 650 nm is advantageous.

The excitation radiation 9 is coupled into the light conductor 3 by means of a separate lens system 2 or by a collimator optical system which in the case of laser diodes is frequently already integrated therein. Such a light conductor may be rigidly or flexibly configured and further may be equipped at its end towards the tooth with further optical means (lenses) for aimed beam guiding and/or may be adapted in its dimensions to the mouth region of the patient and to the tooth to be investigated. Moreover, there may be mounted on or in the light conductor 3 exchangeable deflection mirrors or lenses which facilitate the investigation of the tooth 4. Thus, the employment of the light conductor 3 makes it possible to direct the excitation radiation 9 in an aimed manner to the region 5 of the tooth or of the teeth 4 to be investigated. Thereby, the device in accordance with the invention can be adapted flexibly to the various requirements of everyday practice in the recognition of caries in human teeth (or animal teeth). What has been said with regard to the light conductor 3 applies likewise also for the further light conductor 6, which delivers the fluorescence radiation to the filter 7. The two light conductors 3 and 6 may each have a plurality of Light conducting fibres. In the case of employment of a laser as light source 1, the excitation radiation 9 and the fluorescence radiation 10 can be transmitted via relatively thin light conductor fibres having a core diameter of for example 200 $\mu$m. The employment of two separate light conductors 3 and 6 for the transmission of the excitation radiation 9 and the fluorescence radiation 10 is advantageous in particular for the investigation of external surfaces of the tooth. With the exemplary embodiment illustrated in FIG. 2 the positions of the light conductors 3 and 6 at the tooth can thus be selected independently of one another and individually, which in particular cases makes possible an optimisation of the detection sensitivity for deep lying or very obscurely lying lesions.

The filter 7 of the device in accordance with the invention has a large pass range for wavelengths greater than 670 nm. The filter 7 can be realised for example by means of a coloured glass cut-off filter or other optical elements for spectral selection, e.g. a diffraction grating. The filter should advantageously by so configured that it fluoresces itself as little as possible. As can be seen from FIG. 1, in accordance with the invention the fluorescence spectral range between 670 nm and 800 nm is particularly of interest. Thus, there can be provided if appropriate in series with the filter 7 a further filter which has a cutoff region for the long wavelength range having wavelengths greater than 800 nm. Alternatively, a single filter 7 can also be employed which has a pass-band for wavelengths between 670 nm and 800 nm.

The detection device 8 advantageously has as light sensitive elements photodiodes for detecting the fluorescent radiation. For increasing the sensitivity, the photodiodes may be provided with integrated pre-amplifiers. Likewise, a photomultiplier can be considered as amplifier element in the optical field of the fluorescence radiation 10.

For the case that both the light source 1 and also the light sensitive element of the detection device 8 consist of semiconductor components, for voltage supply of the device in accordance with the invention there can be employed a low voltage mains part, which due to the slight power take-up can consist solely of batteries or rechargeable batteries.

FIG. 3 shows a second exemplary embodiment of the invention whereby the components of the device illustrated in FIG. 2 are provided with identical reference signs. With the exemplary embodiment illustrated in FIG. 3, the fluorescence radiation 10 is transmitted via the same light conductor as the excitation radiation 9. To couple the fluorescence radiation 10 out of the beam output in the light conductor 3 there is provided a beam divider 11 which is arranged between the light source 1 and the lens arrangement 2 or alternatively between the lens arrangement 2 and the end of the light conductor 3 towards the light source. This configuration of the invention is significant in particular for use for the investigation of root canals.

FIG. 4 shows a third exemplary embodiment of the device in accordance with the invention. With this exemplary embodiment although in principle two separated light conductors 2 and 6 are provided for the transmission of the excitation radiation 9 and the fluorescence radiation 10, the light conductor 3 is joined with the light conductor 6 in the form of a handpiece 15, to facilitate handling. The light conductor 6 itself comprehends a plurality of light conductor fibres 6a. Alternatively, the light conductor 3 for transmission of the excitation radiation 9 can also be formed of a plurality of fibres.

FIG. 5 shows a cross-section through the end of the handpiece towards the tooth. Advantageously, the individual light conductors 6a of the light conductor 6 are concentrically arranged around the single fibre of the light conductor 3. In this way reliability and exactitude of detection of the fluorescence radiation can be increased or stabilised.

FIG. 6 shows a side view of the end of the handpiece 15 towards the tooth. As can be seen from FIG. 6, the ends of the light conductor fibres 6a are advantageously chamfered so that—dependent upon the distance of the handpiece 15 from the tooth surface 5 to be investigated—a reliable and extensive overlapping of the excitation radiation 9 and the fluorescence radiation 10 can be achieved.

In FIG. 4 there is illustrated additionally an evaluation device 12 having an indicator or display device 13 coupled thereto. The evaluation device 12 evaluates the data delivered from the detection device 8 and determines the presence or absence of carious tooth regions. The indicator or display device 13 serves for visual representation of the measurement signal delivered from the detection device 8. Likewise an acoustic indication of the measurement signal is conceivable. The evaluation device 12 and/or the display device 13 can be combined into the detection device 8.

A general problem in the recognition of caries, plaque or bacterial infection on teeth with the above-described method is found in that the detected fluorescence radiation can be disruptively superimposed with daylight or the artificial room lighting. This environmental light can likewise be reflected from the tooth and thus collected by the light conducting fibres 6a of the light conductor 6. The spectral region of the environmental light lying in the detection region in accordance with the invention (wavelength greater than 670 nm) then leads to an background signal which restricts the sensitivity of the caries recognition.

This problem can be effectively resolved in accordance with the invention in that the excitation radiation 9 generated by the light source 1 is periodically modulated. Thus, for example, the pulsed generation of the excitation radiation 9 is conceivable. In this case, because of the short duration of the excited state—in the region of nanoseconds—the fluorescence radiation follows the intensity of the excitation radiation practically instantaneously. In contrast, the environmental light is not periodically modulated and is superimposed on the detected fluorescence radiation solely as a constant component. For evaluation of the fluorescence radiation, now only the radiation modulated with the corresponding frequency is employed as detection signal and evaluated. In this way, the constant component of the environmental light is quasi filtered out and the recognition of caries, plaque or bacterial infection is effected virtually independently of the environmental light. Since the environmental light is, however, modulated slightly with the frequency of the mains voltage, there should be chosen as modulation frequency for the excitation radiation 9 a frequency which differs distinctively from the mains voltage frequency and preferably lies in the range between 100 Hz and 200 kHz. With these modulation frequencies, the modulated component of the excitation radiation can be appreciated in a simple manner also acoustically by means of a head set or a loud speaker.

For modulation of the excitation radiation 9 there is represented in FIG. 4 a rotating slit diaphragm 14. This can be replaced by other mechanical kinds of chopper. If a laser diode is employed as light source 1, the modulation of the excitation radiation 9 can be directly brought about by means of corresponding variation of the laser diode voltage.

We claim:

1. A device for the recognition of caries, plaque or bacterial infection on teeth, comprising a light source for generating an excitation radiation which is to be directed onto a tooth to be investigated and producing a fluorescence radiation at the tooth; a detection device for detecting the fluorescence radiation of the tooth; and a spectral filter arranged in front of the detection device, wherein the wavelength of the excitation radiation emitted from the light source lies within the range of between 640 and 670 nm.

2. The device according to claim 1, wherein the wavelength of the excitation radiation is 650 nm.

3. A device for the recognition of caries, plaque or bacterial infection on teeth, comprising a light source for generating an excitation radiation which is to be directed onto a tooth to be investigated and producing a fluorescence radiation of the tooth; a detection device for detecting the fluorescence radiation of the tooth; a first spectral filter arranged in front of the detection device; and a second spectral filter arranged in series with the first spectral filter, wherein the second spectral filter passes radiation having a wavelength of less than 800 nm.

4. A device for the recognition of caries, plaque or bacterial infection on teeth, comprising a light source for generating an excitation radiation which is to be directed onto a tooth to be investigated and producing a fluorescence radiation at the tooth; a detection device for detecting the fluorescence radiation of the tooth; a spectral filter arranged in front of the detection device; and an evaluation device being connected to the detection device, whereby said evaluation device, on the basis of the fluorescence radiation of the tooth detected by the detection device, determines respectively the presence or absence of a carious tooth.

5. A device for the recognition of caries, plaque or bacterial infection on teeth, comprising a light source for generating an excitation radiation which is to be directed onto a tooth to be investigated and producing a fluorescence radiation at the tooth; a detection device for detecting the fluorescence radiation of the tooth; a spectral filter arranged in front of the detection device; and a common light conductor for transmitting the excitation radiation and the fluorescence radiation of the tooth, said common light conductor having at least one light-conducting fiber for transmitting the excitation radiation and a plurality of light-conducting fibers for transmitting the fluorescence radiation.

6. The device according to claim 5, wherein a beam divider is arranged between the light source and an end of the common light conductor towards the light source for coupling out the fluorescence radiation.

7. The device according to claim 5, wherein the light-conducting fibers for transmitting the fluorescence radiation are arranged concentrically about the at least one light-conducting fiber for transmitting the excitation radiation.

8. The device according to claim 7, wherein the ends of the light-conducting fibers for transmitting the fluorescence radiation are chamfered outwardly in a radial direction from the at least one light-conducting fiber transmitting the excitation radiation.

9. The device according to claim 5, wherein the diameter of the light-conducting fibers is about 200 $\mu$m.

* * * * *